United States Patent [19]

Kawakami et al.

[11] 4,139,498
[45] Feb. 13, 1979

[54] PROCESS OF MANUFACTURING HIGH-CONCENTRATION OLEFIN SULFONATE SOLUTION

[75] Inventors: Akira Kawakami, Sakura; Toshiaki Ogoshi, Funabashi; Yoshio Aoki, Tokyo; Masao Honda, Ichikawa, all of Japan

[73] Assignee: The Lion Fat & Oil Co., Ltd., Tokyo, Japan

[21] Appl. No.: 751,164

[22] Filed: Dec. 16, 1976

[30] Foreign Application Priority Data

Dec. 26, 1975 [JP] Japan ................................ 50-154809

[51] Int. Cl.$^2$ ......................... C11D 1/14; C11D 1/83; C11D 3/37; C11D 11/04
[52] U.S. Cl. ..................................... 252/555; 252/156; 252/173; 252/536; 252/DIG. 14; 252/DIG. 15; 260/513 T
[58] Field of Search ........ 252/156, 536, 555, DIG. 14, 252/DIG. 15, 173; 260/513 T

[56] References Cited

U.S. PATENT DOCUMENTS

| 3,376,336 | 4/1968 | Stein | 260/513 T |
| 3,415,753 | 12/1968 | Stein | 252/138 |
| 3,461,159 | 8/1969 | Wendt | 260/513 T |
| 3,755,203 | 8/1973 | Bentley | 252/536 |
| 3,781,339 | 12/1973 | Tuvell | 252/536 |
| 3,954,660 | 5/1976 | Kennedy | 252/353 |
| 3,954,679 | 5/1976 | Wixon | 252/536 |
| 4,003,857 | 1/1977 | Gorsich | 260/513 T |
| 4,014,806 | 3/1977 | Connor | 252/DIG. 14 |

Primary Examiner—Dennis L. Albrecht
Assistant Examiner—Richard Bueker
Attorney, Agent, or Firm—Blanchard, Flynn, Thiel, Boutell & Tanis

[57] ABSTRACT

A process of manufacturing $C_{10}$–$C_{20}$ α-olefin sulfonate solution of high concentration, which comprises subjecting α-olefin sulfonates having 10–20 carbon atoms to neutralization and hydrolysis in the presence of (a) an alkaline material equivalent to the sum (A+B) of an amount of alkali (A) necessary for performing neutralization and hydrolysis of said sulfonates stoichiometrically and an amount of alkali (B) equivalent to 0.2–1.5 times as much as said amount of alkali (A) by weight, (b) an alkylene oxide derivative and/or a polyvinyl alcohol equivalent to 0.2–2 times as much as said amount of alkali (B) by weight, and (c) water necessary for making the water content of the neutralization-hydrolysis product less than 50%.

6 Claims, No Drawings

PROCESS OF MANUFACTURING HIGH-CONCENTRATION OLEFIN SULFONATE SOLUTION

BACKGROUND OF THE INVENTION

The present invention relates to a process of manufacturing olefin sulfonate solution containing α-olefin sulfonates at a high concentration and having a low viscosity.

α-olefin sulfonates useful as the active ingredient of granular heavy duty detergents, etc. are generally manufactured by sulfonating α-olefins having 10 – 20 carbon atoms and subjecting the resulting sulfonates to neutralization and hydrolysis with alkali. In this neutralization-hydrolysis process, water is naturally required and, therefore, the olefin sulfonates product is obtained usually in the form of an aqueous solution. As the process of manufacturing a granular heavy duty detergent containing olefin sulfonates, a process has been adapted which comprises preparing a detergent slurry by admixing this olefin sulfonate solution with other active detergent ingredients as occasion demands and further adding thereto a desired builder, and thereafter subjecting said slurry to spray drying, thereby obtaining a granular heavy duty detergent.

In the case of this conventional process, from the view point of productivity, it is profitable to make the concentration of the solid matters in said detergent slurry as high as possible, provided that handling of the slurry is not inconvenient. Besides, depending on the intended use of said slurry, there are some cases wherein a slurry that does not have a low water content is disqualified for economic or technical reasons, and, from the view point of practical application too, a highly concentrated slurry is advantageous.

However, in the case of manufacturing modern heavy duty granular detergents called KONPACTO SENZAI (which means compacted detergent) or NO-SHUKU SENZAI (which means concentrated detergent) placed on the market in Japan since 1975, it is very advantageous to make high the concentration of the solid matter in said slurry, namely the concentration of nonvolatile materials such as active ingredient, builder and other additives. This compacted granular heavy duty detergent for heavy duty is, to be precise, a detergent whose bulk density is greater than that of conventional granular detergents (that is, the bulk density of conventional granular detergents is in the range of 0.25 – 0.30 in terms of BD, while in the case of this compacted granular detergent, it is more than 0.34) and the amount of detergent necessary for washing is less than that of conventional detergents. Accordingly, it has an advantage that a substantial reduction of the package cost, transport cost and warehouse charge is possible compared with conventional detergents.

Inasmuch as a detergent slurry is, as stated above, generally prepared by adding a desired builder and other detergent additives to an active ingredient solution, in order to prepare a slurry having high concentration of solid matter, it is necessary to employ an active ingredient solution having a high concentration (or low water content). However, in the case of applying olefin sulfonates as said active detergent ingredient, it has been very difficult to manufacture a low-viscosity active ingredient solution having a good workability by the known methods.

In other words, the conventional olefin sulfonate solutions are, as set for above, manufactured through the process wherein olefin sulfonates are neutralized and hydrolyzed by using the stoichiometric alkaline material in an amount necessary for neutralizing and hydrolyzing said olefin sulfonates or a slight excess amount of said alkaline material (typically caustic soda), in the form of an aqueous solution thereof having a concentration of about 7 – 8%. However, in order to obtain a low-viscosity olefin sulfonate solution having a good workability so as not to cause inconvenience in preparing a detergent slurry, the limit of the water content thereof is about 60%, and it is impossible to make the water content below this limit. An olefin sulfonate solution obtained by the conventional process is too high in water content for use as the active ingredient solution used in manufacturing a compacted detergent.

As the means for lowering the water content of an olefin sulfonate solution from common sense, it is conceivable to reduce the amount of the aqueous solution of alkali used in the neutralization-hydrolysis step and to concentrate or dry the olefin sulfonate solution per se. Neither of these procedures can provide an olefin sulfonate solution which fits the purpose of the present invention.

In this connection, according to the process of reducing the amount used of the aqueous alkali solution by increasing the concentration of aqueous alkali solution for use in neutralization-hydrolysis as adopted in the conventional process, the amount of water in the mixture of sulfonates and alkaline material inevitably becomes insufficient so that it is difficult to bring the sulfonates into uniform contact with the alkaline material so as to effect sufficient neutralization and hydrolysis; and even if said neutralization and hydrolysis are effected sufficiently, the resulting product will be of high viscosity and it may gel.

On the other hand, drying or concentrating an olefin sulfonate solution containing about 60% of water as manufactured through the conventional process is uneconomical inasmuch as it necessitates the additional step of drying or concentrating, and not only that, there is a fear that scorching will occur during drying and the viscosity of the solution will increase during concentrating. Therefore, neither the drying step or the concentrating step is advisable.

To sum up, as long as the conventional neutralization-hydrolysis process is followed, it is substantially unfeasible to manufacture, in an economic and industrially satisfactory manner, an olefin sulfonate solution having a low viscosity and which does not interfere with the preparation of a detergent slurry.

SUMMARY OF THE INVENTION

The present invention provides a process of manufacturing an α-olefin sulfonate solution having a low viscosity and containing the α-olefin sulfonates in high concentration. The essence of the process lies in subjecting α-olefin sulfonate to neutralization and hydrolysis in the presence of (a) an alkaline material in an amount equivalent to the sum (A + B) wherein (A) is the stoichiometric amount of alkali necessary for performing neutralization and hydrolysis of said sulfonates and (B) is the amount of alkali equivalent to 0.2 – 1.5 times by weight, of said (A) amount of alkali, (b) an alkylene oxide derivative and/or a polyvinyl alcohol in an amount of 0.2 – 2 times by weight, said (B) amount of alkali, and (c) water necessary for providing the neutralization-hydrolysis product with a water content of less than 50%.

The present inventors have conducted a series of studies on the process of manufacturing a highly concentrated α-olefin sulfonate solution and found that, on the occasion of conducting neutralization and hydrolysis of olefin sulfonates, the use of an alkaline material in an amount in excess of the stoichiometric amount of alkali sufficient for neutralizing and hydrolyzing said olefin sulfonates, together with an alkylene oxide derivative and/or a polyvinyl alcohol, renders it possible to effect neutralization-hydrolysis of the olefin sulfonates uniformly, even if the content of water in the reaction system for effecting the neutralization and hydrolysis is in the range of 25% – 50%. The resulting olefin sulfonate solution will manifest a viscosity of less than 100 poises (at 50° C.) which is no hindrance to the preparation of a detergent slurry. Accordingly, an α-olefin sulfonate solution obtained by the process of the present invention contains α-olefin sulfonates in high concentration and therefore it has an excellent aptitude for use as the active ingredient solution in preparing the aforesaid compacted detergent.

The α-olefin sulfonates for use in the present invention can be easily obtained by sulfonating olefins having 10 – 20 carbon atoms synthesized through Ziegler's reaction and/or wax cracking process, with sulfur trioxide, following the conventional process.

The amount of the alkaline material for use in the neutralization-hydrolysis process under the present invention is, as set forth above, equal to the sum (A+B), wherein (A) is the stoichiometric amount of alkali necessary for performing neutralization and hydrolysis of said sulfonates and (B) is an amount of the alkali equal to 0.2 – 1.5 times by weight, the amount (A) of alkali. When this excess amount (B) of alkali deviates from the foregoing range, the viscosity of the resulting solution will increase excessively. As the alkaline material, any of caustic soda, caustic potash and sodium carbonate is applicable, and these substances can be used either individually or as mixtures. This alkaline material may be added to the olefin sulfonate solution in the solid form, but, in general, it is preferable to apply it in the form of an aqueous solution from operational point of view. In this context, however, the concentration of the alkali aqueous solution and the amount thereof used should of course be determined by taking into due consideration the amount of water specified under (c) above. In general, the concentration of aqueous alkali solution is desirably in the range of 15% – 35% by weight.

The amount of the alkylene oxide derivative and/or polyvinyl alcohol used in the present invention is 0.2 – 2 times by weight, the said excess amount (B) of alkali. The use of an amount less than the lower limit of this range is undesirable because the viscosity of the resulting solution will increase, while in the case of using an amount more than the upper limit of this range, although it is not utterly useless, the effect thereof is not conspicuous and material gain cannot be expected. The term 'alkylene oxide derivative' as used herein means diethylene glycol, polyethylene glycol, polyethylene type non-ionic surface active agent, polypropylene glycol, etc., and particularly polyethylene glycol having a mean molecular weight of 400 – 20,000 or thereabouts and polypropylene glycol having a mean molecular weight of 200 – 6,000 or thereabouts are preferable as the alkylene oxide derivative for use in the present invention. As the polyvinyl alcohol, one whose polymerization degree is in the range of 500 – 2,000 is suitable.

According to the above described neutralization-hydrolysis under the present invention, an olefin sulfonate solution containing olefin sulfonates at a high concentration of more than 60% can be obtained while ensuring a low viscosity of 20 – 80 poises or thereabouts (at 50° C.) which will not interfere with the preparation of a detergent slurry. Therefore, according to the process of the present invention, an α-olefin sulfonate solution convenient for manufacturing a compacted detergent can be manufactured through a simple operation.

Hereunder will be explained the constitution and the effect of the present invention in a further concrete form by reference to examples embodying the invention. These examples, however, do not limit the generally broad scope of the present invention.

DESCRIPTION OF THE PREFERRED EMBODIMENTS

EXAMPLE 1.

200 g of sulfonates of α-olefins having 16 – 18 carbon atoms were employed in each experiment. An aqueous alkali solution containing the aforesaid stoichiometric amount (A) of alkali necessary for performing neutralization and hydrolysis of α-olefin sulfonates and the excess amount (B) of said alkali was prepared. The content of water in this aqueous solution was set at an amount necessary for providing the neutralization-hydrolysis product with a water content of 35%.

Next, after pouring the thus prepared aqueous alkali solution in a 0.5 l autoclave equipped with a stirrer, by adding thereto 200 g of said α-olefin sulfonates and further adding alkylene oxide derivative (C), a neutralization reaction was effected for 5 minutes at a temperature of less than 50° C., and then by heating the contents of the autoclave up to 150° C., a hydrolysis reaction was effected for 30 minutes. Subsequently, the reaction product was taken out of the autoclave and the viscosity of product at 40° C., 50° C. and 80° C., respectively was measured by means of a Brookfield-model viscometer (namely, B8H, the manufacture of TOKYO KEIKI K.K.).

The results of measurements of the viscosity of various neutralization-hydrolysis products obtained by modifying in various ways the applied amount (B) of excess alkali and that of the alkylene oxide derivative (C) in experiments conducted by the above procedure were as shown in the following Table-1. In this context, the amount (B) of excess alkali was expressed by the relative ratio (by weight) of said excess amount (B) to the stoichiometric amount (A) of alkali, and the amount of alkylene oxide derivative used was expressed by the relative ratio (by weight) of said amount to the amount (B) of excess alkali.

Table-1

| Experiment No. | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| sulfonate C distribution [mean molecular weight] | | | | | | | | | | | | $C_{16}$–$C_{18}$ [317] | | | | | |

Table-1-continued

| Experiment No. | | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|---|
| alkali | applied amount name of alkali for neutralization | | | | | | | | | | | | 200 g NaOH | | | | | |
| | applied amount of alkali (A) | | | | | | | | | | | | 27.6 g | | | | | |
| | name of excess alkali | | | | | | | | | | | | NaOH | | | | | |
| | applied amount of excess alkali (B/A) | 0.15 | | | 0.22 | | | | | 0.38 | | | 1.47 | | | | | 1.8 |
| alkylene oxide derivative | name of substance (C) [mean molecular weight] | | | | | | | | | | | | polyethylene glycol [6,000] | | | | | |
| | applied amount (C/B) | 1.0 | 0.08 | 0.23 | 1.0 | 1.9 | 3.0 | 0.08 | 0.23 | 1.0 | 1.9 | 3.0 | 0.08 | 0.23 | 1.0 | 1.9 | 3.0 | 1.0 |
| water content | | | | | | | | | | | | | | 35% | | | | |
| viscosity (poise) | 40° C | 1,200 | 900 | 70 | 50 | 80 | 400 | 1,000 | 70 | 40 | 50 | 500 | 1,100 | 80 | 60 | 75 | 1,300 | 1,200 |
| | 50° C | 800 | 450 | 50 | 40 | 70 | 320 | 400 | 55 | 30 | 40 | 260 | 380 | 60 | 50 | 65 | 600 | 700 |
| | 80° C | 500 | 400 | 30 | 30 | 50 | 280 | 200 | 40 | 25 | 35 | 220 | 290 | 50 | 45 | 50 | 300 | 400 |

EXAMPLE 2.

α-olefin sulfonates were neutralized and hydrolyzed through the same procedure as in Example 1 save for applying various aqueous alkali solutions so adjusted as to make the water contents of the neutralization-hydrolysis products 25%, 35% and 48%, respectively, and the viscosities of the resulting various products were measured. The results were as shown in the following Table-2.

Table-2

| | Experiment No. | 18 | 9 | 19 |
|---|---|---|---|---|
| sulfonate | C distribution [mean molecular weight] | $C_{16} - C_{18}$ [317] | | |
| | applied amount | 200 g | | |
| | name of alkali for neutralization | NaOH | | |
| alkali | applied amount of alkali (A) | 27.6 g | | |
| | name of excess alkali | NaOH | | |
| | applied amount of excess alkali (B/A) | 0.38 | | |
| alkylene oxide derivative | name of substance (C) [mean molecular weight] | polyethylene glycol [6000] | | |
| | applied amount (C/B) | 1.0 | | |
| water content | | 25% | 35% | 48% |
| viscosity (poise) | 40° C | 90 | 40 | 25 |
| | 50° C | 75 | 30 | 20 |
| | 80° C | 50 | 25 | 7 |

EXAMPLE 3.

α-olefin sulfonates were neutralized and hydrolyzed through the same procedure as in Example 1 save for modifying the kind of α-olefin sulfonate, the kind and amount of applied alkali, the kind and amount of applied alkylene oxide derivative and the water content of neutralization-hydrolysis product in various ways as shown in the following Table-3, and the viscosities of the resulting various products were measured. The results were as shown in Table-3.

Table-3

| | Experiment No. | 20 | 21 | 22 | 23 | 24 | 25 | 26 |
|---|---|---|---|---|---|---|---|---|
| sulfonate | C distribution [mean molecular weight] | $C_{12}-C_{14}$ [260] | $C_{14}-C_{18}$ [310] | $C_{16}-C_{18}$ [317] | $C_{12}-C_{18}$ [306] | $C_{16}-C_{18}$ [317] | $C_{14}-C_{18}$ [310] | $C_{12}-C_{14}$ [260] |
| | applied amount | 200 g | | | | | | |
| | name of alkali for neutralization | NaOH | | | | | | |
| alkali | applied amount of alkali (A) | 33.2 g | 28.2 g | 27.6 g | 26.8 g | 27.6 g | 28.2 g | 33.2 g |
| | name of excess alkali | KOH | $Na_2CO_3$ | NaOH | KOH | $Na_2CO_3$ | NaOH | KOH |
| | applied amount of excess alkali (B/A) | 0.61 | 0.7 | 0.38 | 0.61 | 0.70 | 0.38 | 0.70 |
| alkylene oxide derivative | name of substance (C) | PEG [400] | PEG [20,000] | DEG | PVA | PPG [2,000] | NPE | LAE |
| | applied amount (C/B) | 0.38 | 0.55 | 1.8 | 0.63 | 0.33 | 1.0 | 0.55 |
| water content | | 35% | | 30% | 40% | 35% | 40% | |
| viscosity (poise) | 40° C | 90 | 70 | 60 | 45 | 50 | 50 | 80 |
| | 50° C | 50 | 60 | 30 | 45 | 60 | 40 | 60 |
| | 80° C | 35 | 50 | 25 | 40 | 80 | 35 | 40 |

(Remarks)
PEG: polyethylene glycol
DEG: diethylene glycol
PVA: polyvinyl alcohol (polymerization degree = 1,500)
PPG: polypropylene glycol
NPE: nonyl phenol ethoxylate (mean mol number of added ethylene oxide = 8)
LAE: lauryl alcohol ethoxylate (mean mol number of added ethylene oxide = 11)

What is claimed is:

1. In a process of manufacturing an aqueous olefin sulfonate solution which comprises neutralizing and hydrolyzing the reaction product obtained by sulfonating α-olefin having from 10 to 20 carbon atoms, the improvement which comprises:

the neutralizing and hydrolyzing steps are performed in the presence of (a) an alkaline material in an amount equal to the sum of amount A plus amount B, wherein amount A is the stoichiometric amount of said alkaline material for effecting neutralization and hydrolysis of said reaction product and amount B is equal to from 0.2 to 1.5 times the amount A;
(b) polyvinyl alcohol having a polymerization degree in the range of 500 to 2000, wherein the amount of said polyvinyl alcohol is from 0.2 to 2.0 times the amount (B) of said alkaline material, and
(c) water in an amount effective to make the water content of the product of the neutralizing and hydrolysis steps less than 50%.

2. A process according to claim 1 wherein said alkaline material is selected from the group consisting of NaOH, KOH, $Na_2CO_3$ and mixtures thereof.

3. A process according to claim 1 wherein said alkaline material is applied in the form of an aqueous solution containing 15 to 35 percent by weight of said alkaline material.

4. In a process of manufacturing an aqueous olefin sulfonate solution which comprises neutralizing and hydrolyzing the reaction product obtained by sulfonating α-olefin having from 10 to 20 carbon atoms, the improvement which comprises:
the neutralizing and hydrolyzing steps are performed in the presence of
(a) an alkaline material in an amount equal to the sum of amount A plus amount B, wherein amount A is the stoichiometric amount of said alkaline material for effecting neutralization and hydrolysis of said reaction product and amount B is equal to from 0.2 to 1.5 times the amount A;
(b) a substance selected from the group consisting of polyethylene glycol having a mean molecular weight in the range of about 400 to about 2000 and polypropylene glycol having a mean molecular weight in the range of about 200 to about 6000, wherein the amount of said substance is from 0.2 to 2.0 times the amount (B) of said alkaline material, and
(c) water in an amount effective to make the water content of the product of the neutralizing and hydrolysis steps less than 50%.

5. A process according to claim 4 wherein said alkaline material is selected from the group consisting of NaOH, KOH, $Na_2CO_3$ and mixtures thereof.

6. A process according to claim 4 wherein said alkaline material is applied in the form of an aqueous solution containing 15 to 35 percent by weight of said alkaline material.

* * * * *

UNITED STATES PATENT AND TRADEMARK OFFICE
CERTIFICATE OF CORRECTION

PATENT NO. : 4 139 498
DATED : February 13, 1979
INVENTOR(S) : Akira Kawakami et al It is certified that error appears in the above—identified patent and that said Letters Patent are hereby corrected as shown below:

Column 8, line 11; change "2000" to ---20000---.

Signed and Sealed this

Fifth Day of June 1979

[SEAL]

Attest:

RUTH C. MASON
Attesting Officer

DONALD W. BANNER
Commissioner of Patents and Trademarks